United States Patent [19]

Ross

[11] 4,082,339
[45] Apr. 4, 1978

[54] SOFT CONTACT LENS INSERTION AND REMOVAL INSTRUMENT

[76] Inventor: Joseph Ross, 14335 Sherman Way, Apt. 202, Van Nuys, Calif. 91405

[21] Appl. No.: 816,703

[22] Filed: Jul. 18, 1977

[51] Int. Cl.² ............................................... A61F 9/00
[52] U.S. Cl. .................................. 294/1 CA; 294/99 R
[58] Field of Search .................. 294/1 CA, 33, 99 R; 51/216 LP, 217 L; 81/43; 128/303 R, 321; 206/5.1; 351/160

[56] References Cited
U.S. PATENT DOCUMENTS

| 2,919,696 | 1/1960 | Rinaldy | 294/1 CA X |
| 3,063,083 | 11/1962 | Obitts | 294/1 CA UX |
| 3,139,298 | 6/1964 | Grabiel | 294/1 CA |
| 4,026,591 | 5/1977 | Cleaveland | 294/1 CA |

Primary Examiner—Johnny D. Cherry
Attorney, Agent, or Firm—Poms, Smith, Lande & Glenny

[57] ABSTRACT

A non-suction cup-type instrument for the insertion and removal of soft contact lenses is made of surgical rubber. It includes a central portion which looks somewhat like a suction cup having two sides cut away, and has small wedge-shaped contact lens-engaging elements or members protruding inwardly from each side of this suction cup-like member. It is again particularly noted that no suction cup action is involved in the present instrument. The instrument is also provided with two resilient arms which are aligned with the wedge-shaped contact lens engaging elements and which may be employed to support these elements and hold the lens more firmly once they are engaged. The space between the two wedge-shaped contact lens-engaging members, which incidentally have an overall configuration corresponding to opposed segments of a circle, is such that they are spaced apart by slightly less than the diameter of a contact lens.

14 Claims, 5 Drawing Figures

U.S. Patent
April 4, 1978
4,082,339
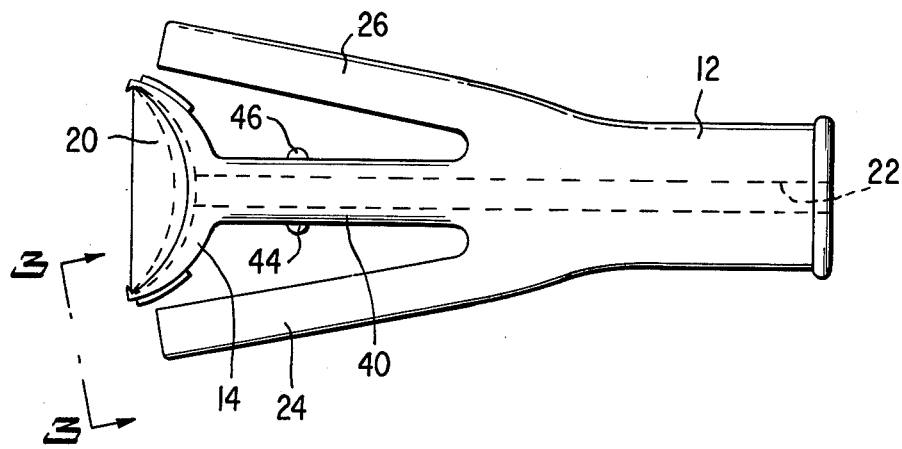
Fig. 1
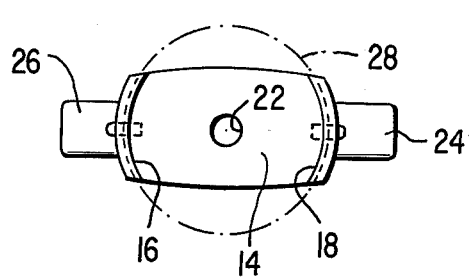
Fig. 2
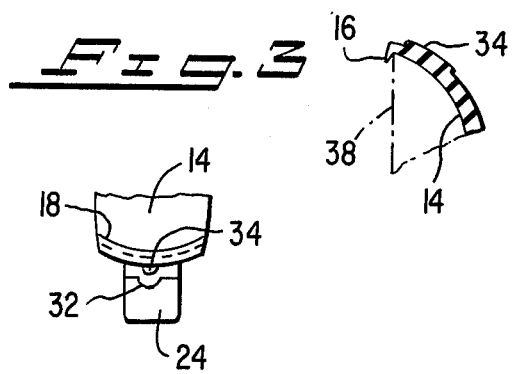
Fig. 3
Fig. 4
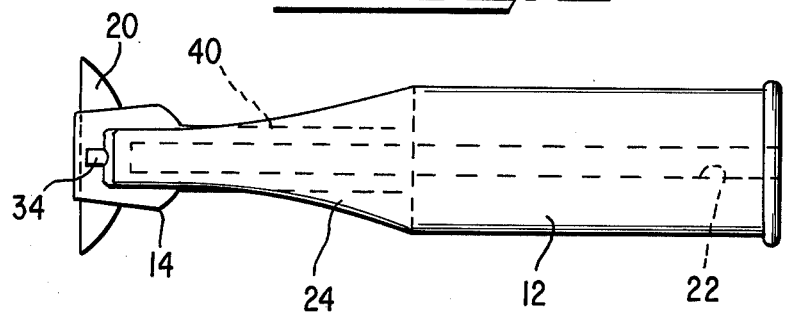
Fig. 5

SOFT CONTACT LENS INSERTION AND REMOVAL INSTRUMENT

FIELD OF THE INVENTION

This invention relates to contact lens insertion and removal instruments, and more specifically to such instruments for use with soft type contact lenses.

BACKGROUND OF THE INVENTION

By way of historical background, hard contact lenses were developed in the late 1940's, gained national prominence in the early 1950's and grew steadily in usage until they have exceeded ten million pairs per year by the 1960's and early 1970's. Since the introduction of the hard contact lens, ophthalmologists and optometrists have taught and used only one method of insertion and removal of hard contact lenses. More specifically, the method of insertion is to place the lens on the end of a finger, such as the index finger, bring the lens to the eye and inserting, while the other hand spreads the eye open. Removal of the hard lens merely requires pulling the outer edge of the upper eyelid taut and blinking rapidly, if necessary. The hard lens would then fall into the user's open palm or onto a towel.

Only ten percent to fifteen percent of those attempting to learn the procedure outlined above failed. And these prospective users were then merely informed that they could not wear contact lenses. Most of the persons failing were older persons whose upper eyelid would not eject the lens, or those whose hands were subject to shaking so that they could not smoothly insert the lenses. All mechanical methods were and are, for the most part, shunned by optometrists and ophthalmologists, since practically all include methods of suction being applied to the contact lens which can severely injure the eye. Typical disclosures showing various suction devices of the type mentioned above include W. Henning, U.S. Pat. No. 3,600,028; R. S. Boone, U.S. Pat. No. 3,791,689; A. Rinaldy, U.S. Pat. No. 2,919,696 and E. H. Carruthers, U.S. Pat. No. 3,934,914.

There was little problem with bacteria in connection with hard contact lenses, and particularly with the insertion and removal thereof, as the hard lenses were not porous, and did not readily pick up bacteria, and the only point of contact with the human hand was between the center of the outside of the hard contact lens and the ball of one finger. As will be developed below, however, the soft contact lens presents a much more serious problem relative to bacteria, particularly with regard to the insertion and removal of these soft lenses.

Soft lenses became nationally known in late 1973. They have come into increasing use since then, and would probably be much more widely used except for the bacteria and infection problems which are particularly pronounced in connection with the insertion and removal of such lenses. More specifically, the soft lens is porous, and requires more finger handling and contact to remove from the case mount and involves much more contact with the fingers as it is much like a thin soaked piece of paper and there is therefore much more opportunity for transferring finger contamination to the eye. Even more serious is the problem of removal since two fingers must be applied to the eye near the opposing edges of the lens, and these two fingers must be moved toward one another so that the lens is squeezed and removed. This is particularly difficult for women who may have long fingernails which may easily contact the eye and scratch its surface. Also, the chance that dirt under fingernails will contact the eye is greatly increased. As a collateral matter, regardless of the care exercised, the soft lenses may be easily damaged by finger handling and must be discarded upon such damage, a matter of several hundred dollars in expense.

As a result of the difficulties in handling soft contact lenses, more than 25% of the normal prospective users are unable to insert and remove such lenses on a regular basis.

It is again noted that the principal approach up to the present time with regard to the insertion and removal of contact lenses has been the suction cup concept. Unfortunately, in order to apply sufficient force to remove contact lenses with a suction cup, sufficiently great force must be applied to the contact lens that the eye may be seriously and permanently damaged. Accordingly, as mentioned above, virtually no ophthalmologists or optometrists recommend any mechanical devices for inserting or removing contact lenses.

A principal object of the present invention is to provide a solution to the foregoing problem, i.e. to provide a non-suction cup-type instrument for the insertion and removal of soft contact lenses which will not damage nor infect the eye.

SUMMARY OF THE INVENTION

In accordance with a preferred embodiment of the invention, a delicate instrument for inserting and removing soft contact lenses includes a pair of wedge-shaped contact lens engaging elements which have an overall configuration of diametrically opposed segments of the circumference of a circle. These wedge-shaped elements are made of very soft resilient material, and have a normal spacing slightly less than the diameter of a soft contact lens. A resilient mount is provided so that, with a contact pressure against the eye of less than a gram, the elements will spread slightly to encompass the edge of the contact lens. Backup support members are then brought into play to firmly hold the engaging elements against the opposite edges of the soft contact lens as it is being removed.

In accordance with a collateral feature of the invention, all of the parts of the soft contact lens removing instrument may be made of very soft synthetic rubber material of a non-porous and high temperature resistant type.

In accordance with another subordinate feature of the invention, the instrument may be provided with a central aperture for optical alignment of the center of the instrument with the eye, as the soft contact lenses are inserted or removed.

In accordance with an additional feature of the invention, the soft contact lens instrument may be molded integrally with three arms, one for supporting the two wedge-shaped contact lens engaging members, and the other two for providing backup support following engagement of these wedge-shaped members with the soft contact lens, as it is being picked up and transported from the case to the eye of vice-versa.

In accordance with a feature of the invention, the normal separation of the contact lens engaging elements for members may be in the order of about 12 millimeters in its relaxed or unbiased state, as compared with the 12½ millimeter diameter of the normal soft contact lens. Upon application of slight pressure on the instrument in engagement with the eye or the holder for the soft contact lens, the two wedge-shaped engaging elements separate by a millimeter or so to encompass the outer periphery of the soft contact lens. Then, as they are supported by bringing the two outer arms into engagement with the support for the lens-engaging elements, the edges of the soft contact lens are picked up and sealing engagement between the eye and the soft contact lens is broken so that it may be easily removed.

In accordance with another feature of the invention, the wedge-shaped contact lens engaging elements from an acute angle with the plane of the circle which defines the position of the two lens-engaging elements.

In accordance with a broad aspect of the invention, a delicate instrument for inserting and removing soft contact lenses includes a pair of resilient elements for engaging the opposite edges of a soft contact lens, with the normal spacing between said resilient elements being slightly less than the diameter of the soft contact lens. Then, upon the application of a force less than 1 gram into engagement with the soft contact lens, the resilient elements expand to encompass and engage the outer edges of the lens. Thereafter, holding means are brought into play to move these engaging elements inwardly and firmly yet softly break the seal between the soft contact lens and the eye, followed by removal of the soft contact lens. By this technique, the initial contact with the soft contact lens is resilient and has a force of less than 1 gram, while the subsequent bringing in of the backup supporting members permits firm removal despite the initial very soft placement of the instrument into its proper position.

Other objects, features, and advantages of the invention will become apparent from a consideration of the following detailed description and from the accompanying drawings.

BRIEF DESCRIPTION OF THE DRAWINGS

FIG. 1 is a top view of an illustrative instrument for inserting and removing soft contact lenses;

FIG. 2 is a front end view of the instrument of FIG. 1;

FIG. 3 is a fragmentary oblique view taken along lines III—III of FIG. 1;

FIG. 4 is an enlarged cross-section of the portion of the instrument which actually engages the edge of the soft contact lens; and FIG. 5 is a side view of the instrument.

DETAILED DESCRIPTION OF THE DRAWINGS

Referring more particularly to the drawings, FIG. 1 shows an illustrative soft lens insertion and removal instrument, including a main body portion 12 and a front contact lens receiving assembly 14. The soft contact lens receiving assembly 14 includes as two critical elements the outer wedge-shaped contact lens engaging members or elements 16 and 18. These elements fit over the outer circumference of the contact lens 20 and retain it in the overall assembly 14. The instrument of FIG. 1 is provided with a central aperture 22 which is useful in the optical alignment of the instrument of FIG. 1 in the course of inserting or removing soft lenses 20 from the eye. This type of opening 22 is known per se. The two arms 24 and 26 engage the assembly 14 and provide more firm support which is desirable in the course of actually removing the soft lens and picking it up after it has been engaged by the wedge-shaped tips 16 and 18.

FIG. 2 is a front end view of the instrument shown in FIG. 1. As clearly shown in FIG. 2, the lens engaging elements 16 and 18 are opposite segments of a circle 28, which has been drawn in dashed lines for convenience in discussing the geometric configuration.

Incidentally, it is useful to clearly distinguish the present soft contact lens handling instrument from the dangerous suction type devices which present a not inconsiderable danger of damage to the human eye. In the present case, as shown in FIG. 2, the contact lens receiving assembly 14 is not completely circular as in the case of suction cups, but only extends for a portion of the area of a circle, including, as mentioned above, the opposed segments of the circumference of the circle 28 along which the elements 16 and 18 lie.

FIG. 3 is a fragmentary oblique view taken along lines III—III of FIG. 1. Particularly to be noted in FIG. 3 are the groove 32 in the arm 24 and the matching ridge 34 on the underside of the lens-receiving assembly 14. This matching groove and ridge serve to keep the flexible or resilient arms 24, 26, aligned with and in engagement with the contact lens holding assembly 14, and insure direct application of force between these members.

FIG. 4 is an enlarged cross-sectional view showing the configuration and orientation of the wedge-shaped contact lens engaging element 16 and its relationship to the remainder of the lens holding assembly 14. It may be noted in passing that the plane of the circle 28, as shown in FIG. 2, is indicated by the vertical dashed line 38 in FIG. 4. It may also be noted that the wedge-shaped soft contact lens engaging element 16 makes an angle of approximately 30° with the plane 38 of the circle 28 as shown in FIG. 2. Accordingly, when the instrument is advanced toward the eye to remove a soft contact lens, upon the slight expansion of the tips 16 and 18, when lightly pressed against the lens on the eye, these tips engage the outer edges of the lens. This step is preparatory to the application of firm additional pressure by arms 24 and 26, through which the contact lens is released from and may be removed from the eye. Incidentally, to indicate the order of the dimensions which are involved, the instrument shown in the drawings is approximately 1⅛ inches in length and the space between contact lens engaging elements 16 and 18, as mentioned above, is approximately 12 millimeters, in the unflexed condition, as compared with the diameter of a contact lens which is normally about 12¼ millimeters in diameter. With a pressure of less than a gram, normally in the order of about one-quarter of a gram, the tips 16 and 18 separate by an additional millimeter or so and encompass the soft lens. Thereafter, as mentioned above, pressure is brought to bear against the outer side of the resilient arms 24 and 26, the wedge-shaped members 16 and 18 pick up the edges of the soft lens, break the seal with the eye, and permit free and easy removal of the soft contact lens.

It is again noted that the acute angle which the tips 16 make with the plane of the circle 38 contributes to this convenient and simple mode of operation, as described above. In FIG. 4, the outer ridge 34 as shown in FIG. 3, may also be noted.

FIG. 5 is a side view of the instrument, and in general includes the elements discussed above. It may be noted, however, that the contact lens 20 may be seen extending above and below the lens-holding assembly 14. Also, the smaller diameter central support 40 for the lens holding assembly 14 is shown in dashed lines behind resilient arm 24 in FIG. 5.

With regard to the material and method of manufacture of the instrument shown in the drawings, it may be molded in one piece from synthetic resilient material. More specifically, successful results have been achieved using a material which is available from Dow Corning Company and which is known as Silastic-E. An equivalent clean grade plastomer which is also available from Dow Corning is known as MDX 4-4210. In the molding of this material, it sets up in 5 minutes at 150° Centigrade. Of course, prior to molding it is mixed with some catalyst material which is also provided by Dow Corning and which is approximately ten percent by volume of the basic Silastic material. This particular material is non-porous and may be boiled for substantial periods of time. For example, it has been boiled for intervals of more than fifteen minutes and was held at a temperature of 450° F. for 5 minutes with no adverse effect on the instrument. The fact that the material will withstand this type of elevated temperature facilitates cleanliness and sterilization to preclude any possibility of bacterial infection.

It may also be noted that, using the instrument of the present invention, the adverse problems mentioned above which are encountered in the course of removal of soft contact lenses are completely avoided. Instead of the possibility of scratching the surface of one's eye, which is particularly dangerous for persons with long fingernails, a very, very light pressure of a fraction of a gram of very soft rubbery material is used in the course of removing the soft lenses. Accordingly, safety has greatly improved and the danger to the eye is significantly reduced. Further, through the use of a sterile instrument, the danger of bacterial infection of the porous soft lens is greatly reduced as compared to the exposure to the usual contamination which is present under fingernails.

Incidentally, while the present device is designed for soft contact lenses having a diameter of approximately 12½ millimeters, it is of course applicable to soft lenses of other sizes, such as the 9½ millimeter soft contact lens size. It would of course be applicable to other sizes, with the only change which is required being the modification of the separation of the lens-engaging tips.

In the foregoing description, emphasis was placed on inserting and removing soft contact lenses from the eye. Another very important aspect involves the removal of the contact lenses from and replacement to their mounts or pads in the carrying cases. Incidentally, of course all soft lens carrying cases are filled with the proper solution of salt and water to keep the lens soft and properly flexible for insertion in the eye. In removing a soft lens from its pad, the device of the present invention is (1) placed on the lens on the pad, (2) slight pressure is applied to expand member 14 so that tips 16 and 18 will overlie the edges of the lens, (3) then the arms 24 and 26 are gently squeezed and the lens is removed from the pad. In step (4) the arms are then released so that the lens springs fully open but is held by the cup and the tips 16 and 18. The device, holding the lens is placed in front of the eye, with the lids held open by the fingers of the other hand, with the narrow or cutaway part of the cup at the top and bottom. With eyesight focused through aperture 22, the eye is touched with the lens. The lens will cling to the eye, and is already properly centered. During this insertion the device is held only by the handle 12 and the arms 24 and 26 are not touched. In the removal process, after removing the lens from the eye, the pressure on the arms 24 and 26 is released; then the lens is touched to the pad and remains there as the cup is lifted away.

Concerning an additional structural aspect of the invention, stops 44 and 46 may be provided (see FIG. 1) to limit the movement of arms 24 and 26, respectively, so that the soft lens will not be deformed unduly.

In closing, it is evident that minor changes may be made in the present invention without departing from the spirit and scope thereof. By way of example and not of limitation, the pressure supplied by arms 24 and 26 could be provided by separate rigid elements which might be hinged to the main body of the instrument, instead of by the integrally molded arms 24 and 26 as shown. Other minor mechanical changes are of course within the scope of the present invention.

What is claimed is:

1. A delicate instrument for inserting and removing soft or flexible-type contact lenses, comprising:
a resilient soft contact lens holder, said holder including
a pair of wedge-shaped contact lens engaging members, said engaging members having the overall configuration of diametrically opposed segments of the circumference of a circle, with said wedge-shaped members pointing inwardly and at an acute angle above the plane of said circle; and resilient means interconnecting said two wedge-shaped lens engaging members and making an acute angle with respect to said lens engaging members, said resilient interconnecting means providing a range of movement for said lens engaging means extending from separation slightly more than the diameter of a soft contact lens, to a holding position with a separation slightly less than the diameter of said soft lens;
means for supporting said soft lens holder; and
means for selectively maintaining said lens engaging members in the holding positions, or releasing said lens engaging members from said holding position.

2. An instrument as defined in claim 1 wherein said lens holder includes means for providing a rest position for said wedge-shaped contact lens engaging members which is approximately equal to the diameter of a soft contact lens, and for opening to a slightly larger diameter to pick up said soft lens upon pressure against the eye of less than one gram.

3. An instrument as defined in claim 1 wherein said instrument is made of surgical rubber.

4. An instrument as defined in claim 1 wherein said supporting means is provided with a central aperture for aligning said instrument with the center of the eye when inserting or removing soft lenses.

5. An instrument as defined in claim 1 wherein said means for maintaining said lens-engaging members in the holding position includes two resilient arms secured to said supporting means.

6. An instrument as defined in claim 5 wherein means are provided for aligning each said arm to apply inwardly directed radial pressure substantially to the center of each said lens-engaging member.

7. An instrument as defined in claim 1 wherein the entire instrument is a single molding of synthetic resilient material.

8. An instrument as defined in claim 1 wherein said wedge-shaped soft lens engaging members have an extent of less than one-sixteenth of an inch.

9. An instrument as defined in claim 1 wherein said resilient means interconnecting said soft lens engaging members has a curvature greater than the normal curvature of the convex side of a soft contact lens.

10. A delicate instrument for handling soft contact lenses comprising:
 resilient means for engaging the opposite edges of a soft contact lens, and resilient means including two engagement elements normally spaced apart by a distance slightly less than the diameter of a soft contact lens, and said resilient means including support means for expanding the distance between said elements by the application of a force of less than one gram; and
 holding means for increasing the inward force on said engagement elements to free the lens from the eye, thereby permitting initial location of the engagement elements with negligible force, followed by firm removal of the soft lens from the eye.

11. An instrument as defined in claim 10 wherein said holding means includes two arms, and means are provided for aligning each said arm to apply inwardly directed radial pressure substantially to the center of each said lens-engagement element.

12. An instrument as defined in claim 11 wherein stop means are provided for limiting the movement of said arms and for correspondingly limiting the flexure of the soft lens.

13. An instrument as defined in claim 10 wherein the entire instrument is a single molding of synthetic resilient material.

14. An instrument as defined in claim 13 wherein said resilient material is non-porous and high temperature resistant.

* * * * *